US00PP26647P2

(12) United States Plant Patent
Zaiger et al.

(10) Patent No.: US PP26,647 P2
(45) Date of Patent: Apr. 26, 2016

(54) NECTARINE TREE NAMED 'ATOMIC RED'

(50) Latin Name: ***Prunus persica* var. *nucipersica***
Varietal Denomination: Atomic Red

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 23 days.

(21) Appl. No.: 14/121,932

(22) Filed: Nov. 6, 2014

(51) Int. Cl.
*A01H 5/08* (2006.01)

(52) U.S. Cl.
USPC ..... Plt./188

(58) Field of Classification Search
USPC ..... Plt./188
CPC ..... A01H 5/0856
See application file for complete search history.

*Primary Examiner* — Kent L Bell

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium size fruit.
3. Fruit with an attractive red skin color.
4. Fruit with firm, white flesh.
5. Fruit with good flavor and eating quality, with a good balance between acid and sugar.

1 Drawing Sheet

Botanical designation: *Prunus persica* var. *nucipersica*.
Variety denomination: 'Atomic Red'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Arctic Queen' Nectarine (U.S. Plant Pat. No. 8,094), 'Honey Kist' Nectarine (U.S. Plant Pat. No. 9,333) and our proprietary non-patented nectarine seedling selections '112LH324' and '151LE81'.

STATEMENT REGARDING FEDERALLY SPONSORED RESEARCH AND DEVELOPMENT

Not applicable.

ORIGIN OF THE VARIETY

The new and distinct variety of nectarine tree (*Prunus* var. *nucipersica*) was developed by us in our experimental orchard located near Modesto, Calif. from open pollinated seed collected from our proprietary non-patented nectarine seedling selection with the field identification number '112LH324'. The seed, parent (112LH324) originated from open pollinated seed collected from our proprietary non-patented nectarine seedling selection '151LE81' which originated from open pollinated seed collected from 'Arctic Queen' (U.S. Plant Pat. No. 8,094). A large number of these open pollinated seedlings were planted and maintained on their own root system, during which time we recognized the desirable tree and fruit characteristics of the present seedling and selected it in 1997 for additional asexual propagation and commercialization.

ASEXUAL REPRODUCTION OF THE VARIETY

In 1997 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a regular and productive bearer of medium size, white flesh, clingstone fruit. The fruit is further characterized by its attractive dark red skin color and good flavor and eating quality. In comparison to the proprietary non-patented nectarine seed parent '112LH324' the fruit of the new variety has a more attractive dark red skin color. In comparison to its ancestor 'Arctic Queen' Nectarine (U.S. Plant Pat. No. 8,094) the fruit of the new variety is approximately 23 days earlier in maturity. In comparison to the commercial variety 'Honey Kist' Nectarine (U.S. Plant Pat. No. 9,333) the fruit of the new variety has white flesh compared to yellow and is approximately 14 days later in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 17 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 17 year old specimens grown near Modesto, Calif., with color in accordance with Munsell Book of Color published in 1958.

Tree:

*Size*.—Large, usually pruned to 3 to 3.5 meters in height and width for economical harvesting of fruit, varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 30°, increases with heavy crop load.

*Productivity*.—Productive, thinning and spacing necessary for desired market size fruit. Number of fruit set varies with climatic conditions during blooming period.

*Bearer*.—Regular, has had adequate fruit set 15 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium. Average circumference 54.5 cm at 25.4 cm above ground on a 17 year old tree.

*Stocky*.—Medium stocky.

*Texture*.—Medium shaggy, roughness increases with age.

*Color*.—2.5Y 4/2.

Branches:

*Size*.—Medium. Average circumference 18.5 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 24 in a 25.8 square cm area. Average length 4.7 mm. Average width 2.5 mm. Color 5Y 6/2.

*Color*.—New growth varies from 5GY 6/6 to 5GY 5/8. Mature growth varies from 10YR 5/2 to 10YR 3/4, varies with age of growth.

Leaves:

*Size*.—Medium to large. Average length 126.5 mm. Average width 36.2 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 8.8 mm. Average width 1.6 mm. Longitudinally grooved. Surface — glabrous. Color varies from 2.5GY 6/8 to 2.5GY 5/8.

*Glands*.—Type — reniform. Size — medium. Average length 1.2 mm. Average diameter 0.8 mm. Average number 3, varies from 2 to 4. Located primarily on the base of the leaf blade and the upper portion of the petiole. Color varies from 7.5Y 5/6 to 7.5Y 7/6.

*Stipules*.—Average number 2. Average length 5.3 mm. Edges — pectinate. Color varies from 2.5GY 6/8 to 2.5YR 2/4.

*Color*.—Upper surface varies from 5GY 4/4 to 7.5GY 4/2. Lower surface varies from 5GY 5/4 to 5GY 4/4. Midvein color varies from 2.5GY 7/4 to 2.5GY 8/4.

Flower buds:

*Size*.—Medium. Average length 17.4 mm. Average diameter 10.2 mm.

*Hardiness*.—Hardy with respect to California winters.

*Density*.—Medium.

*Form*.—Conical, becoming elongated just before opening.

*Pedicel*.—Average length 3.2 mm. Average width 1.7 mm. Surface — glabrous. Color varies from 2.5GY 6/8 to 5GY 6/6.

*Color*.—Varies from 10RP 4/14 to 10RP 4/12.

Flowers:

*Blooming period*.—Date of First Bloom Feb. 14, 2014. Date of Petal Fall Feb. 24, 2014, varies slightly with climatic conditions.

*Size*.—Large, showy. Average height 18.8 mm. Average diameter 41.7 mm.

*Petals*.—Number — double flowered, varies from 10-12. Form — elliptical. Petal apex — rounded. Petal base — acuminate. Size — large. Average length 20.0 mm. Average width 14.7 mm. Arrangement — overlapping. Margin — sinuate. Color varies from 10RP 5/12 to 7.5RP 4/10, color fades with age of flower. Both upper and lower surfaces glabrous.

*Sepals*.—Number — 5 to 6. Size — medium to large. Average length 5.2 mm. Average width 4.8 mm. Shape — ovate. Margin — entire. Surface — upper surface glabrous, lower surface pubescent. Colors — upper surface varies from 10Y 8/4 to 2.5GY 8/4. Lower surface varies from 5R 3/6 to 7.5R 3/4.

*Stamens*.—Average number per flower 49. Average filament length 14.8 mm. On average, the stamens are even with the height of the petals. Filament color N 9.5/(white) to 7.5RP 5/12. Anther color varies from 5Y 8/8 to 7.5R 3/2.

*Pollen*.—Self fertile. Color varies from 5Y 8/8 to 5Y 8.5/8.

*Pistil*.—Number — normally one. Average length 16.5 mm. Position of stigma an average of 1.6 mm below anthers. Surface — glabrous. Color varies from 7.5Y 7/8 to 7.5Y 7/6.

*Fragrance*.—Heavy.

*Color*.—Varies from 7.5RP 5/12 to 5RP 5/12.

*Number flowers per flower bud*.—Normally one.

*Pedicel*.—Average length 3.5 mm. Average width 1.7 mm. Surface — glabrous. Color varies from 2.5GY 6/8 to 5GY 6/6.

Fruit:

*Maturity when described*.—Firm ripe and ready for consumption.

*Date of first picking*.—Jul. 1, 2014.

*Date of last picking*.—Jul. 11, 2014, varies slightly with climatic conditions.

*Size*.—Medium. Average diameter axially 61.6 mm. Average transversely in suture plane 68.6 mm. Average weight 153.4 grams, varies slightly with fertility of the soil, amount of thinning and climatic conditions.

*Form*.—Globose.

*Suture*.—Nearly smooth, extends from base to apex.

*Ventral surface*.—Smooth to slightly lipped.

*Apex*.—Rounded to slight tip.

*Base*.—Retuse.

*Stem cavity*.—Rounded to slightly elongated in suture plane. Average depth 6.8 mm. Average diameter 7.4 mm.

Stem:

*Size*.—Small. Average length 8.7 mm. Average diameter 3.5 mm.

*Color*.—Varies from 10Y 6/8 to 2.5GY 5/8.

Flesh:

*Ripens*.—Evenly.

*Texture*.—Firm, meaty, crisp.

*Fibers*.—Few, small, tender.

*Firmness*.—Firm, comparable to other commercial varieties.

*Aroma*.—Slight.

*Amydgalin*.—Undetected.

*Eating quality*.—Good.

*Flavor*.—Good, with a good balance between acid and sugar.

*Juice*.—Moderate amount, enhances flavor.

*Acidity*.—Not available.

*Brix*.—Average Brix 11.1°, varies slightly with amount of fruit per tree and climatic conditions.

*Pit cavity*.—Average length 35.2 mm. Average width 27.5 mm. Average depth 12.5 mm. Color varies from 7.5Y 8/4 to 5R 3/10.

*Color*.—Varies from 5Y 8.5/4 to 7.5Y 9/4.

Skin:

*Thickness*.—Medium.

*Surface*.—Smooth.

*Pubescence*.—Wanting.

*Tendency to crack*.—None.

*Color*.—Ground color varies from 7.5Y 9/2 to 7.5Y 9/4. Overspread with 7.5R 3/10 to 7.5R 2/6.

*Tenacity*.—Tenacious to flesh.

*Astringency*.—Undetected.

Stone:

*Type*.—Clingstone, strong adherence.

*Size*.—Large: Average length 34.2 mm. Average width 26.5 mm. Average thickness 22.9 mm.

*Form*.—Ovoid.

*Base*.—Flat.

*Apex*.—Pointed. Average length 2.1 mm.

*Surface*.—Pitted throughout.

*Sides*.—Unequal, one side extending further from suture plane.

*Ridges*.—Small, narrow ridge extending from base toward apex.

*Tendency to split*.—None.

*Color*.—Varies from 7.5YR 5/8 to 10YR 5/8 when dry.

Kernel:

*Size*.—Medium. Average length 18.0 mm. Average width 12.6 mm. Average depth 7.1 mm.

*Form*.—Ovoid.

*Viability*.—Viable, complete embryo development.

*Skin color*.—Varies from 5Y 9/4 to 7.5Y 9/4.

Use:

*Dessert*.—Market — local and long distance.

Keeping quality: Good, held firm in cold storage for 3 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

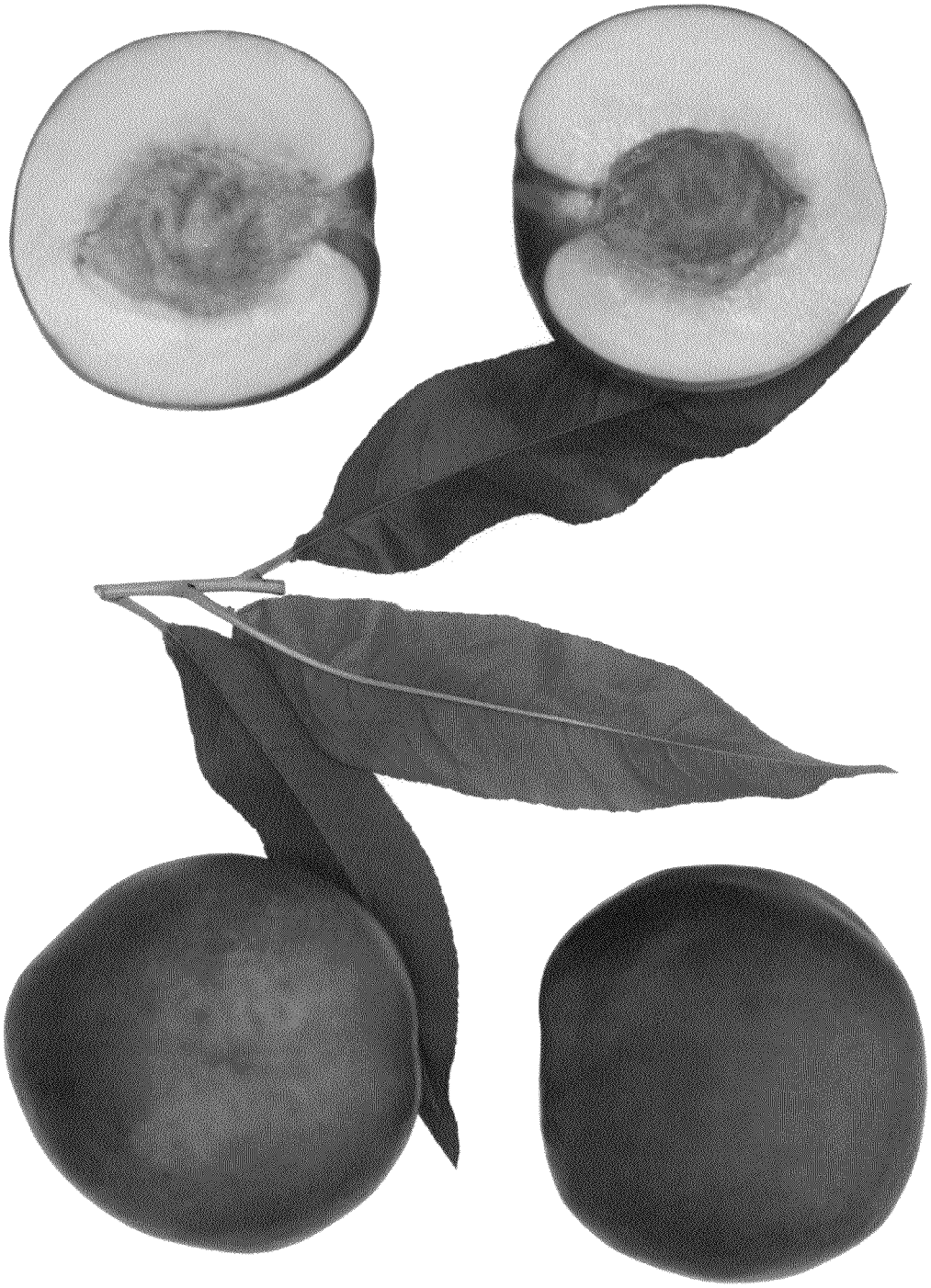

* * * * *